United States Patent
Pollard

(10) Patent No.: US 9,492,438 B2
(45) Date of Patent: Nov. 15, 2016

(54) AMPHIPHILIC PYRIDINUM COMPOUNDS TO TREAT EPILEPSY AND OTHER DISORDERS OF THE NERVOUS SYSTEM

(71) Applicant: Bette Pollard, Potomac, MD (US)

(72) Inventor: Bette Pollard, Potomac, MD (US)

( * ) Notice: Subject to any disclaimer, the term of this patent is extended or adjusted under 35 U.S.C. 154(b) by 0 days.

(21) Appl. No.: 14/808,650

(22) Filed: Jul. 24, 2015

(65) Prior Publication Data

US 2016/0022656 A1 Jan. 28, 2016

Related U.S. Application Data

(60) Provisional application No. 62/029,149, filed on Jul. 25, 2014.

(51) Int. Cl.
*A61K 31/4425* (2006.01)
*A61K 31/216* (2006.01)
*A61K 31/5375* (2006.01)

(52) U.S. Cl.
CPC ......... *A61K 31/4425* (2013.01); *A61K 31/216* (2013.01); *A61K 31/5375* (2013.01)

(58) Field of Classification Search
IPC .................................................. A61K 31/4425
See application file for complete search history.

(56) References Cited

U.S. PATENT DOCUMENTS 7,893,094 B2 * 2/2011 Pollard ................ C07D 213/20
514/358

OTHER PUBLICATIONS

Diaz et al. (Procedings of Nat. Acasemy of Sciences; 106(9) 3348-3353; (2009).*
Palop (Nat Neurosci. Jul. 2010 ; 13(7): 812-818).*
Noebels (Epilepsia. Jan. 2011 ; 52(Suppl 1): 39-46).*
Li et al. (Seizure 20 (2011) 249-256).*
Billiau et al, "Intravenous Immunoglobulins in Refractory Childhood-onset Epilepsy: Effects on Seizure Frequency, EEG Activity, and Cerebrospinal Fluid Cytokine Profile," Epilepsia, 48(9):1739-1749, 2007.
Castillo-Caranza et al, "Tau Immunotherapy Modulates Both Pathological Tau and Upstream Amyloid Pathology in an Alzheimer's Disease Mouse Model," The Journal of Neuroscience, Mar. 25, 2015 • 35(12):4857-4868.
Choi et al, "Cellular injury and neuroinflammation in children with chronic intractable epilepsy," Journal of Neuroinflammation 2009, 6:38.
De Herdt et al, "Effects of vagus nerve stimulation on pro- and anti-inflammatory cytokine induction in patients with refractory epilepsy," (Journal of Neuroimmunology 214 (2009) 104-108.
Devinsky et al, "Glia and epilepsy: excitability and inflammation," Trends in Neurosciences, Mar. 2013, vol. 36, No. 3.
During et al, "Extracellular hippocampal glutamate and spontaneous seizure in the conscious human brain," Lancet 1993, 341, pp. 1607-1670.
E. Jaeger, "Know the Differences between Seizures, Epilepsy & Mimics," J. of Emergency Medicine, Dec. 10, 2012, pp. 2 to 13.
Ko et al, "Epileptiform Discharges," http://emedicine.medscape.com/article/1138880-overview#showall, Apr. 2, 2014 (last visited Jun. 28, 2016).
Koppel et al, "CB2 Receptor Deficiency Increases Amyloid Pathology and Alters Tau Processing in a Transgenic Mouse Model of Alzheimer's Disease," Molecular Medicine 2 0, pp. 29-36 , 2014.
Lauren et al, "Transcriptome Analysis of the Hippocampal CA1 Pyramidal Cell Region after Kainic Acid-Induced Status Epilepticus in Juvenile Rats," May 2010, vol. 5, Issue 5, pp. 1 to 15.
Onos et al, "Toward more predictive genetic mouse models of Alzheimer's disease," Brain Research Bulletin 122 (2016) 1-11.
Palop et al, "Epilepsy and cognitive impairment in Alzheimer's Disease," Arch. Neurol. 66:435-440, 2009.
Poirier et al, "Enhanced dentate gyrus synaptic plasticity but reduced neurogenesis in a mouse model of amyloidosis," Neurobiology of Disease 40 (2010) 386-393.
Pollard et al, "TheTARC/sICAM5 ratio in patient plasma is a candidate biomarker for drug resistant epilepsy,"Frontiers in Neurology, Jan. 2013, vol. 3, Article 181, pp. 1 to 7.
Shi et al, "Cumulative effects of the ApoE genotype and gender on the synaptic proteome and oxidative stress in the mouse brain," International Journal of Neuropsychopharmacology (2014), 17, 1863-1879.
Teng et al, "Low Plasma ApoE Levels Are Associated with Smaller Hippocampal Size in the Alzheimer's Disease Neuroimaging Initiative Cohort," Dement Geriatr Cogn Disord 2015;39:154-166.
Tchilibon et al, "TyAmphiphilic pyridinium salts block TNFa/NFkB signaling and constitutive hypersecretion of Interleukin-8 (IL-8) from cystic fibrosis lung epithelial cells," J. Biochemical Pharmacology 70, (2005), pp. 381-393.
Youn et al, "Serial examination of serum IL-8, IL-10 and IL-1Ra levels is significant in neonatal seizures induced by hypoxic-ischaemic encephalopathy.," (abstract) Scand. J. Immunol., Sep. 2012, 76(3), pp. 286-293.

* cited by examiner

*Primary Examiner* — Shirley V Gembeh
(74) *Attorney, Agent, or Firm* — Walter Ottesen, P.A.

(57) ABSTRACT

A pharmaceutical composition including an amphiphilic pyridinium compound for treating neurological disorders or seizure disorders, in particular epilepsy, and other disorders of the nervous system. The pharmaceutical composition may be used as a primary treatment or as an adjuvant treatment. Administration of the amphiphilic pyridinium compound(s) may occur prior to the manifestation of symptoms characteristic of epilepsy, such that epilepsy is prevented, or alternatively, delayed in its progression.

11 Claims, No Drawings

AMPHIPHILIC PYRIDINUM COMPOUNDS TO TREAT EPILEPSY AND OTHER DISORDERS OF THE NERVOUS SYSTEM

CROSS REFERENCE TO RELATED APPLICATION

This application claims benefit of provisional application 62/029,149, filed Jul. 25, 2014, the entire content of which is incorporated herein by reference.

FIELD OF THE INVENTION

The present invention relates to the use of amphiphilic pyridinium salts and compounds, for the purpose of the treatment of seizure disorders such as epilepsy, temporal lobe epilepsy, drug resistant temporal lobe epilepsy, partial onset seizures, refractory partial seizures, tonic clonic seizures, and other types of seizure disorders, as well as other neurological disorders such as but not limited to migraines, neuralgia, such as but not limited to post herpetic neuralgia, neuronal cancers, obesity, anxiety disorders, schizophrenia, manic-depressive disorder, depression and major depressive disorder, and as an analgesic for relief from pain. It is also proposed that this drug can be used as an adjuvant therapy in combination with standard drugs to treat the disorder, such as standard anti-epileptic drugs (SAEDs).

BACKGROUND OF THE INVENTION

Epilepsy is a group of neurological disorders characterized by epileptic seizures. It is a chronic condition of the brain. It is a complex chronic neurological disorder presented in a vast set of diseases that may not have any obvious cause, and is characterized by spontaneous recurrence surges of cortical nerve cell electrical activity in the brain resulting in unprovoked seizures. It is thought the prevalence is about 50 million people worldwide. The Centers for Disease Control and Prevention (CDC) estimate there are around 2.2 million people in the US with epilepsy. The incidence is about 48 of every 100,000 people. Thus, 150,000 people will develop epilepsy in their lifetime. Drug therapy remains ineffective for seizure control in about 30% of patients because either the drugs do not control the seizures or the patients cannot tolerate the side effects.

The seizures episodes can vary from brief and nearly undetectable to long periods of vigorous shaking. In epilepsy, seizures tend to recur and have no immediate underlying cause, while seizures that occur due to a specific cause are not deemed to represent epilepsy. The cause may be a result of brain injury, stroke, brain tumor, drug or alcohol abuse. Genetic mutations are linked to a small proportion of the disease. The diagnosis typically involves ruling out other conditions that might cause similar symptoms such as fainting, and determining if other causes are present such as alcohol withdrawal or electrolyte problems. This may be done by imaging the brain and performing blood tests. Epilepsy can often be confirmed with an electroencephalogram (EEG) but a normal test does not rule out the condition.

Seizures are controllable with medication in about 70% of cases. Some have seizures that do not respond to medication, surgery, neurostimulation or dietary changes, such as the Ketogenic diet. Not all cases are lifelong.

About 60% of seizures are convulsive. Generalized seizures affect both hemispheres of the brain, and account for ⅓ of the cases. Partial seizures (also called focal seizures), affect one hemisphere of the brain in ⅔ of cases, and may then progress to generalized seizures. The other 40% are non-convulsive. For example, there may be an absence seizure (petit mal), a decreased level of consciousness which usually lasts about 10 seconds. About 6% of people have seizures that are triggered by specific stimuli, such as flashing lights and sudden noises. Some seizures occur during sleep. Only about 25% of people with seizures have epilepsy.

Partial seizures are often preceded by an aura. They may include sensory (visual, hearing or small), psychic, autonomic, or motor phenomena. Jerking may start in a specific muscle group and spread to surrounding muscle groups. Non-consciously generated activities and simple repetitive movements like smacking of the lips may occur.

There are six main types of generalized seizures: tonic-clonic, tonic, clonic, myoclonic, absence, and atonic seizures. Generalized seizures all involve loss of consciousness and typically happen without warning.

Tonic-clonic seizures (grand mal) present with a contraction of the limbs followed by their extension along with arching of the back which lasts 10-30 seconds (the tonic phase). A cry may be heard. Then a shaking of the limbs occurs in unison (clonic phase). Tonic seizures produce constant contractions of the muscles. A person may turn blue from stoppage of breathing. After shaking stops, it may take 10-30 minutes (postictal state) for person to return to normal. There may be loss of bowel or bladder control. The tongue may be bitten.

Myoclonic seizures involve spasms of muscles in either a few areas or all over. Absence seizures can be subtle with only a slight turn of the head or eye blinking. Then the person returns to normal. Atonic seizures involve the loss of muscle activity for more than one second, typically on both sides of the body.

Temporal lobe epilepsy is a chronic neurological condition characterized by recurrent, unprovoked epileptic seizures which originate in the temporal lobe of the brain. They involve sensory changes, such as smelling an unusual odor, or a memory disturbance. The most common cause is mesial temporal sclerosis. Treatment is medication or surgery. Partial seizures account for about 60% of all adult cases. Temporal lobe epilepsy (TLE) is the single most common form of partial seizure.

There is mesial temporal lobe epilepsy (MTLE) arising in the hippocampus, the parahippocampal gyms and the amygdala. The other more rare type, lateral temporal lobe (LTLE), arises in the neocortex at the outer (lateral) surface of the temporal lobe. Autosomal dominant Lateral Temporal Lobe Epilepsy (ADLTLE) is a rare hereditary condition.

Temporal lobe epilepsy and Drug resistant temporal lobe epilepsy is associated with a proinflammatory phenotype in the brain and blood, manifest by activation of the NFκB signaling pathway, and resulting in downstream elevation of proinflammatory cytokines and chemokines such as interleukin-1-beta (IL-1β), interleukin-8 (IL-8) and others (Pollard et al, 2013). Mounting evidence suggests that normal damage control processes in astrocytes and glial cells may contribute to a feed forward loop that promotes epileptic activity (Devinsky et al, 2013; Eisenstein, 2014). Neuronally driven pathological electrical activity may activate the glial cells. Once activated, proinflammatory mediators secreted by the glia may initiate a signaling cascade in neurons that renders them more sensitive to glutamate-induced excitation (During and Spencer, 1993). The inflammatory response may also disrupt the blood-brain-barrier, releasing proinflammatory cytokines and chemokines into the general circulation (Librizzi L, et al. 2012).

The likely involvement of a proinflammatory phenotype for epilepsy has also been implicated in several other recent studies. For example, chronic stimulation of the vagus nerve has been shown to reduce the frequency of adverse events in refractory epilepsy (De Herdt et al, 2009). High levels of various proinflammatory mediators, including IL-8, have been found in surgical excisions of epileptic foci in brains from children with intractable epilepsy (Choi et al. 2009). Injections of kainic acid into the hippocampus to induce seizure activity in rats has resulted in elevated levels of proinflammatory mediators in the rat brain (Lauren et al 2010). In the case of neonatal seizures, elevated levels of proinflammatory mediators have been found in serum (Youn et al, 2012).

Amphiphilic pyridinium compounds have been shown to block TNRα/NFκB signaling and downstream interleukin-8 (IL-8) secretion from cells in vitro (Tchilibon et al. 2005). Optimal inhibitory activities were observed for MRS2481 and its optical isomer MRS2485. These compounds also block the neurotoxic calcium channels formed by amyloid beta peptide (Abeta[1-40]) in neuronal membranes, and protect neurons from Abeta[1-40] dependent cell death (Diaz J C, et al, 2009). Thus these amphiphilic pyridinium compounds have been considered from the vantage point of candidate Alzheimer's Disease drugs. Temporal lobe epilepsy and Drug resistant temporal lobe epilepsy have also been associated with some degree of cognitive impairment, as well as a proinflammatory phenotype.

SUMMARY OF THE INVENTION

The present invention is directed to the use of amphiphilic pyridinium compounds for treating epilepsy and related neurological disorders.

TABLE 1

Structures of pyridinium compounds prepared for testing.

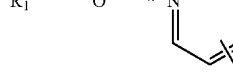

a. 1-20      21, 22

| $R_1$ | Compound | n | $IC_{50}$ |
|---|---|---|---|
| 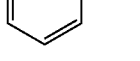 | 1, MRS 2572<br>2, MRS 2573<br>3, MRS 2481<br>4, MRS 2574 | 4<br>6<br>8<br>10 | >30<br>>30<br>1.81 ± 0.58<br>2.52 0.39 |
| 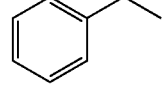 | 5, MRS 2485 | 8 | >25 |
| 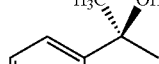 | 6, MRS 2515 | 8 | >30 |
| 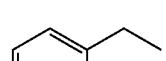 | 7, MRS 2480 | 8 | 12 ± 0.8 |
|  | 8, MRS 2591 | 8 | 3.16 ± 0.52 |
| 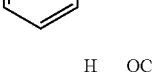 | 9, MRS 2506 | 8 | >30 |

TABLE 1-continued
Structures of pyridinium compounds prepared for testing.
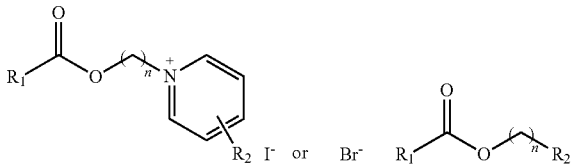
| R₁ | | Compound | R₂ = | IC₅₀ |
|---|---|---|---|---|
| | | 10, MRS 2507 | 8 | >30 |
| | | 11, MRS 2513 | 8 | >30 |
| | | 12, MRS 2514 | 8 | >30 |
| | | 13, MRS 2516 | 8 | >30 |
| | | 14, MRS 2590 | 8 | Toxic at 1 μM |
| | | 15, MRS 2390 | 8 | 2.2 ± 0.8 |
| | | 16, MRS 2517 | 8 | 4.6 ± 0.9 |
| | | 17, MRS 2518 | 8 | >30 |
Compounds with R₂ ≠ H
| R₁ | Compound | R₂ = | IC₅₀ |
|---|---|---|---|
| | 18, MRS 2589 | 3-CONH₂ | 5.56 ± 0.98 |

TABLE 1-continued

Structures of pyridinium compounds prepared for testing.

| | | | |
|---|---|---|---|
| a. 1-20 | | 21, 22 | |
| | 19, MRS 2421 | p-(CH$_2$)$_2$CH$_3$ | 3.3 ± 0.5 |
| | 20, MRS 2423 | p-(CH$_2$)$_2$—OH | 18 ± 0.9 |
| | 21, MRS 2422 | | 24 ± 1.0 |
| | 22, MRS 2391 | | >30 |

BRIEF DESCRIPTION OF THE TABLES

Table 1 illustrates the structures of the Amphiphilic pyridinium salts.

Table 2 illustrates the anticonvulsant properties of MES of MRS2481.

Table 3 illustrates the anticonvulsant properties of 6 Hz of MRS2481.

Table 4 illustrates the anticonvulsant properties of 6 Hz by MRS2485.

DETAILED DESCRIPTION OF THE INVENTION

The following detailed descriptions are presented to enable a person skilled in the art to make and use the invention. For purposes of explanation, specific nomenclature is set forth to provide a thorough understanding of the present invention. However, it will be apparent to one skilled in the art that these specific details are not required to practice the invention. Descriptions of specific applications are provided only as representative examples. Various modifications in the preferred embodiments will be readily apparent to one skilled in the art, and the general principals defined herein may be applied to other embodiments and applications without departing from the scope of the invention. The present invention is not intended to be limited to the embodiments shown, but is to be accorded the widest possible scope consistent with the principals and features disclosed herein.

In one embodiment the amphiphilic pyridinium compounds of Table 1 are administered to a mammal for the treatment of epilepsy.

In another embodiment the amphiphilic pyridinium compounds of Table 1 are administered to a mammal for the treatment of epilepsy using one or more of the pyridinium salts shown in Table 1, in which X$^-$ is an anion, such as iodide, bromide, acetate, halide, mesylate, oxylate, etc, to form an acceptable salt. Although not pyridinium salts, compounds 21 (MRS 2422) and 22 (MRS 2391) are also within the scope of the class of compounds disclosed herein.

Another aspect of the invention provides a method for preventing epilepsy in a mammal by administering to a mammal a therapeutically effective amount of one or more amphiphilic pyridinium compound(s) of the present invention. Administration of the amphiphilic pyridinium compound(s) may occur prior to the manifestation of symptoms characteristic of epilepsy, such that epilepsy is prevented, or alternatively, delayed in its progression.

The term "therapeutically effective amount," as used herein, is that amount that achieves at least partially a desired therapeutic or prophylactic effect in the brain. The amount of amphiphilic pyridinium compound necessary to bring about prevention and/or therapeutic treatment of epilepsy, or related condition, is not fixed per se. An effective amount is necessarily dependent upon the identity and the form of the pyridinium compound employed, the extent of the protection needed, or the severity of the epilepsy condition. The terms amphiphilic and Amphiphilic are used interchangeably herein.

In conjunction with the prophylactic or therapeutic treatment, pharmacogenomics (i.e., the study of the relationship between an individual's genotype and the individual's response to a foreign compound or drug) may be considered. Differences in metabolism of therapeutics can lead to severe toxicity or therapeutic failure by altering the relation between dose and blood concentration of the pharmacologically active drug. Thus a physician or a clinician may consider applying knowledge obtained in relevant pharmacogenomics studies in determining whether to administer an amphiphilic pyridinium compound as well as tailoring the dosage and/or therapeutic regimen of treatment with an amphiphilic pyridinium compound.

Pharmacogenomics deals with clinically significant hereditary variations in the response to drugs due to altered drug disposition and abnormal action in affected persons. In general, two types of pharmacogenetic conditions can be differentiated. Genetic conditions transmitted as a single factor altering the way drugs act on the body (altered drug action) or genetic conditions transmitted as single factors altering the way the body acts on drugs (altered drug metabolism). These pharmacogenetic conditions can occur either as rare genetic defects or as naturally-occurring polymorphisms. For example, glucose-6-phosphate dehydrogenase deficiency (G6PD) is a common inherited enzymopathy in which the main clinical complication is haemolysis after ingestion of oxidant drugs (anti-malarials, sulfonamides, analgesics, nitrofurans) and consumption of fava beans.

One pharmacogenomics approach to identifying genes that predict drug response, known as a "genome-wide association," relies primarily on a high-resolution map of the human genome consisting of already known gene-related sites (e.g., a "bi-allelic" gene marker map which consists of 60,000-100,000 polymorphic or variable sites on the human genome, each of which has two variants). Such a high-resolution genetic map can be compared to a map of the genome of each of a statistically substantial number of subjects taking part in a Phase II/III drug trial to identify genes associated with a particular observed drug response or side effect. Alternatively, such a high resolution map can be generated from a combination of some ten-million known single nucleotide polymorphisms (SNPs) in the human genome. As used herein, a "SNP" is a common alteration that occurs in a single nucleotide base in a stretch of DNA. For example, a SNP may occur once per every 1000 bases of DNA. A SNP may be involved in a disease process. However, the vast majority of SNPs may not be disease associated. Given a genetic map based on the occurrence of such SNPs, individuals can be grouped into genetic categories depending on a particular pattern of SNPs in their individual genome. In such a manner, treatment regimens can be tailored to groups of genetically similar individuals, taking into account traits that may be common among such genetically similar individuals. Thus, mapping of the amphiphilic pyridinium compounds of the invention to SNP maps of patients may allow easier identification of these genes according to the genetic methods described herein.

Alternatively, a method termed the "candidate gene approach," can be utilized to identify genes that predict drug response. According to this method, if a gene that encodes a drug target is known, all common variants of that gene can be fairly easily identified in the population and it can be determined if having one version of the gene versus another is associated with a particular drug response.

As an illustrative embodiment, the activity of drug metabolizing enzymes is a major determinant of both the intensity and duration of drug action. The discovery of genetic polymorphisms of drug metabolizing enzymes (e.g., N-acetyltransferase 2 (NAT 2) and cytochrome P450 enzymes CYP2D6 and CYP2C19) has provided an explanation as to why some subjects do not obtain the expected drug effects or show exaggerated drug response and serious toxicity after taking the standard and safe dose of a drug. These polymorphisms are expressed in two phenotypes in the population, the extensive metabolizer and poor metabolizer. The prevalence of a poor metabolizer phenotypes is different among different populations. For example, the gene coding for CYP2D6 is highly polymorphic and several mutations have been identified in poor metabolizers, which all lead to the absence of functional CYP2D6. Poor metabolizers of CYP2D6 and CYP2C19 quite frequently experience exaggerated drug response and side effects when they receive standard doses. If a metabolite is the active therapeutic moiety, poor metabolizers show no therapeutic response, as demonstrated for the analgesic effect of codeine mediated by its CYP2D6-formed metabolite morphine. The other extreme are the so called ultra-rapid metabolizers who do not respond to standard doses. Recently, the molecular basis of ultra-rapid metabolism has been identified to be due to CYP2D6 gene amplification. Alternatively, a method termed the "gene expression profiling" can be utilized to identify genes that predict drug responses. For example, the gene expression of an animal dosed with a drug (e.g., in response to an amphiphilic pyridinium compound of the present invention) can give an indication whether gene pathways related to toxicity have been turned on.

Information generated from more than one of the above pharmacogenomics approaches can be used to determine appropriate dosage and treatment regimens for prophylactic or therapeutic treatment of an individual. This knowledge, when applied to dosing or drug selection, can avoid adverse reactions or therapeutic failure and thus enhance therapeutic or prophylactic efficiency when treating a mammal with an amphiphilic pyridinium compound.

The invention is further directed to pharmaceutical compositions comprising one or more amphiphilic pyridinium compound(s) of the present invention and a pharmaceutically acceptable carrier.

As used herein the language "pharmaceutically acceptable carrier" is intended to include any and all solvents, solubilizers, fillers, stabilizers, binders, absorbents, bases, buffering agents, lubricants, controlled release vehicles, diluents, emulsifying agents, hemectants, dispersion media, coatings, antibacterial or antifungal agents, isotonic and absorption delaying agents, penetration enhancers, and the like, compatible with pharmaceutical administration. The use of such media and agents for pharmaceutically active substances is well-known in the art. Except insofar as any conventional media or agent is incompatible with the active compound, use thereof in the compositions is contemplated. Supplementary agents can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine; propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates and agents for the adjustment of tonicity such as sodium chloride or dextrose. pH can be adjusted with acids or bases, such as hydrochloric acid or sodium hydroxide. The parenteral preparation can be enclosed in ampoules, disposable syringes or multiple dose vials made of glass or plastic. The subcutaneous application can optionally be enhanced by co-administering a penetration enhancer, such as DMSO.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the injectable composition should be sterile and should be fluid to the extent that easy syringability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol.)

EXAMPLES

Example 1

Demonstration that the Amphiphilic Pyridinium Salt MRS2481 Mitigates a Model of Epilepsy 1.1(a) First Test for MRS2481 on the Animal Model:

The model used is the Maximal Electro-Shock (MES) test in mice. Briefly, the MES is a model for generalized tonic-clonic seizures and provides an indication of a compound's ability to prevent seizure spread when all neuronal circuits in the brain are maximally active. These seizures are highly reproducible and are electrophysiologically consistent with human seizures. For all tests based on MES convulsions, 60 Hz of alternating current (50 mA in mice and 150 mA in rats) was delivered for 0.2 s by corneal electrodes which have been primed with an electrolyte solution containing an anesthetic agent (0.5% tetracaine HCl). Mice or rats were tested at various intervals following doses of 30, 100 and 300 mg/kg of test compound given by i.p. injection or through oral dosing (p.o.). Other doses can be used if indicated by previously known pharmacology or to determine an ED50. An animal was considered "protected" from MES-induced seizures upon abolition of the hindlimb tonic extensor component of the seizure (Swinyard et al., 1989; White et al., 1995a; White et al., 1995b).

1.1(b) Conditions and controls: Compounds were injected into mice at 30 and 100 mg/kg, and assayed at 30 minutes.

1.1(c) Data

TABLE 2

Protection of animals from convulsant MES by MRS2481

| Dose | Time: 30 minutes |
|---|---|
| 100 mg/kg | 1 of 4 animals protected |

1.2.1 (a) Second Type of Animal Model Test for MRS2481:

Some clinically useful AEDs are ineffective in the standard MES and scMET tests but still have anticonvulsant activities in vivo. In order to identify potential AEDs with this profile, compounds may be tested in the minimal clonic seizure (6 Hz or 'psychomotor') test (Barton et al., 2001). Like the maximal electroshock (MES) test, the minimal clonic seizure (6 Hz) test is used to assess a compound's efficacy against electrically induced seizures but uses a lower frequency (6 Hz) and longer duration of stimulation (3 s). Test compounds were pre-administered to mice via i.p. injection. At varying times, individual mice (four per time point) were challenged with sufficient current delivered through corneal electrodes to elicit a psychomotor seizure in 97% of animals (32 mA for 3 s) (Toman et al., 1952). Untreated mice displayed seizures characterized by a minimal clonic phase followed by stereotyped, automatistic behaviors described originally as being similar to the aura of human patients with partial seizures. Animals not displaying this behavior are considered protected. The test was evaluated quantitatively by measuring the responses at varying doses at a determined time of peak effect (TPE).

1.2 (b) Conditions and controls: Compounds were injected into mice at 100 mg/kg, and assayed at 30 minutes.

1.2 (c) Data

TABLE 3

Protection from convulsant 6 Hz by MRS2481

| DOSE | Time: 30 Minutes |
|---|---|
| 100 mg/kg | 2 out of 4 animals protected |

Example 2

Demonstration on Second Compound that Shows the Amphiphilic Pyridinium Salt MRS2485 Mitigates a Model of Epilepsy 2.1(a) animal model: Some clinically useful AEDs are ineffective in the standard MES and scMET tests but still have anticonvulsant activities in vivo. In order to identify potential AEDs with this profile, compounds may be tested in the minimal clonic seizure (6 Hz or 'psychomotor') test (Barton et al., 2001). Like the maximal electroshock (MES) test, the minimal clonic seizure (6 Hz) test is used to assess a compound's efficacy against electrically induced seizures but uses a lower frequency (6 Hz) and longer duration of stimulation (3 s). Test compounds were pre-administered to mice via i.p. injection. At varying times, individual mice (four per time point) were challenged with sufficient current delivered through corneal electrodes to elicit a psychomotor seizure in 97% of animals (32 mA for 3 s) (Toman et al., 1952). Untreated mice displayed seizures characterized by a minimal clonic phase followed by stereotyped, automatistic behaviors described originally as being similar to the aura of human patients with partial seizures. Animals not displaying this behavior are considered protected. The test was evaluated quantitatively by measuring the responses at varying doses at a determined time of peak effect (TPE).

2.1(b) Conditions and controls; Compounds were injected into mice at 30 and 100 mg/kg, and assayed at 30 minutes.

2.1(c) Data

TABLE 4

Protection of animals from convulsant 6 Hz by MRS2485

| Dose | Time: 30 minutes |
|---|---|
| 30 mg/kg | 4 of 4 animals protected |
| 100 mg/kg | 4 of 4 animals protected |

REFERENCES

Pollard J R, Eidelman O, Mueller G P, Dalgard C L, Crino P B, Anderson C T, Brand E J, Burakgazi E, Ivaturi S K, Pollard H B. The TARC/sICAM5 Ratio in Patient Plasma is a Candidate Biomarker for Drug Resistant Epilepsy. *Front Neural.* 2013 Jan. 3; 3:181. doi: 10.3389/fneur.2012.00181. eCollection 2012.

PMID: 23293627

Choi J, Min H J, Shin J S. Increased levels of HMGB1 and pro-inflammatory cytokines in children with febrile seizures. *J Neuroinflammation.* 2011 Oct. 11; 8:135. doi: 10.1186/1742-2094-8-135. PMID: 21989210 [PubMed—indexed for MEDLINE]

De Herdt V, Bogaert S, Bracke K R, Raedt R, De Vos M, Vonck K, Boon P. Effects of vagus nerve stimulation on pro- and anti-inflammatory cytokine induction in patients with refractory epilepsy. *J Neuroimmunol.* 2009 Sep. 29; 214(1-2):104-8. doi: 10.1016/j.jneuroim.2009.06.008. Epub 2009 Jul. 15.

Diaz J C, Simakova O, Jacobson K A, Arispe N, Pollard H B. Small molecule blockers of the Alzheimer Abeta calcium channel potently protect neurons from Abeta cytotoxicity. *Proc Natl Acad Sci USA.* 2009 Mar. 3; 106(9):3348-53. doi: 10.1073/pnas.0813355106. Epub 2009 Feb. 9

Devinsky O, Vezzani A, et al. Glia and epilepsy: excitability and inflammation. Trends in Neurosciences 36:174-184, 2013;

During M J and Spencer D D Extracellular hippocampal glutamate and spontaneous seizure in the conscious human brain. Lancet 341:1607-1610, 1993

Eisenstein M. Unrestrained Excitement Nature 511:S4-S6, 2014).

Laurén H Bl, Lopez-Picon F R, Brandt A M, Rios-Rojas C J, Holopainen I E. Transcriptome analysis of the hippocampal CA1 pyramidal cell region after kainic acid-induced status epilepticus in juvenile rats. PLoS One. 2010 May 20; 5(5):e10733. doi: 10.1371/journal.pone.0010733

Librizzi L, et al. Seizure induced brain-born inflammation sustains seizure recurrence and blood-brain-barrier damage. *Ann. Neurol.* 72:82-90, 2012).

Swinyard E A, Woodhead J H, White H S and Franklin M R (1989) General principles: experimental selection, quantification, and evaluation of anticonvulsants, in Antiepileptic Drugs (R. H. Levy R H M, B. Melrum, J. K. Penry and F. E. Dreifuss ed) pp 85-102, Raven Press, New York;

Tchilibon S, Zhang J, Yang Q, Eidelman O, Kim H, Caohuy H, Jacobson K A, Pollard B S, Pollard H B. Amphiphilic pyridinium salts block TNF alpha/NF kappa B signaling and constitutive hypersecretion of interleukin-8 (IL-8) from cystic fibrosis lung epithelial cells. *Biochem Pharmacol.* 2005 Aug. 1; 70(3):381-93. PMID: 15963954 [PubMed—indexed for MEDLINE]

White H S, Johnson M, Wolf H H and Kupferberg H J (1995a) The early identification of anticonvulsant activity: role of the maximal electroshock and subcutaneous pentylenetetrazol seizure models. Ital J Neurol Sci 16:73-7.

White H S, Woodhead J H and Franklin M R (1995b) General principles: experimental selection, quantification, and evaluation of antiepileptic drugs, in Antiepileptic Drugs (Levy R H M, R. H.; Meldrum, B. S. ed) pp 99-110, Raven Press, New York.

Youn Y Al, Kim S J, Sung I K, Chung S Y, Kim Y H, Lee I G. Serial examination of serum IL-8, IL-10 and IL-1Ra levels is significant in neonatal seizures induced by hypoxic-ischaemic encephalopathy *Scand J Immunol.* 2012 September; 76(3):286-93. doi: 10.1111/j.1365-3083.2012.02710.x

The invention claimed is:
1. A method of treating epilepsy or related condition in a mammal comprising:
administering to the mammal a therapeutically effective amount of a pharmaceutical composition including:

an amphiphilic pyridinium compound selected from the group consisting of

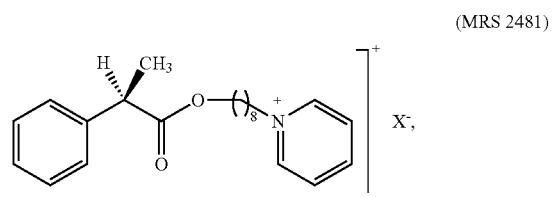
(MRS 2481)

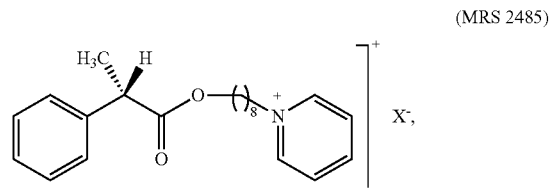
(MRS 2485)

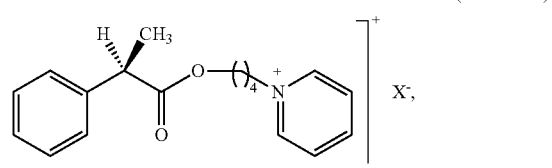
(MRS 2572)

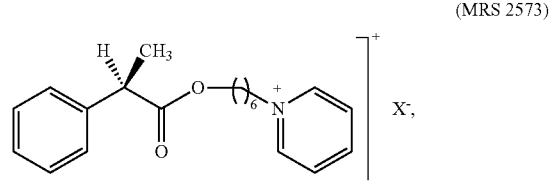
(MRS 2573)

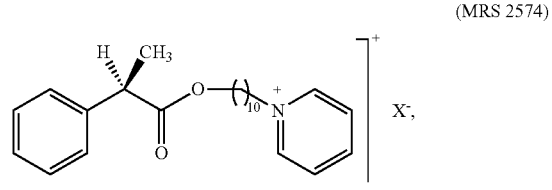
(MRS 2574)

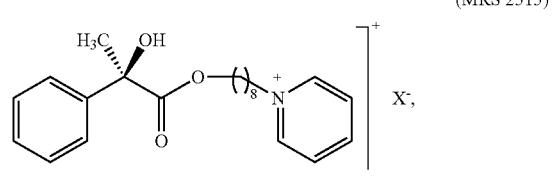
(MRS 2515)

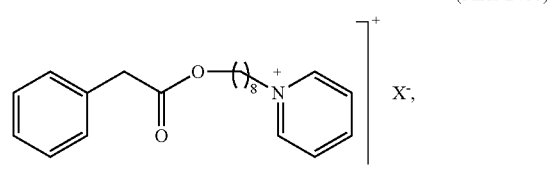
(MRS 2480)

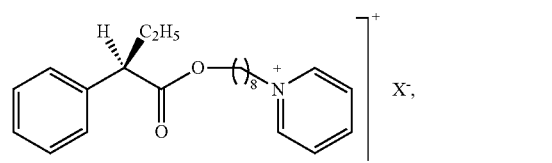
(MRS 2591)

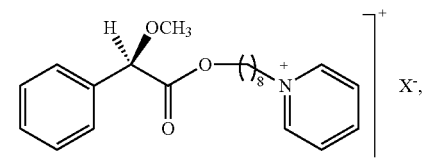
(MRS 2506)
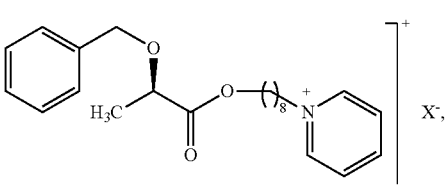
(MRS 2507)
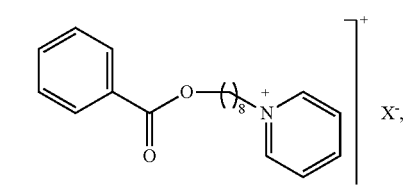
(MRS 2513)
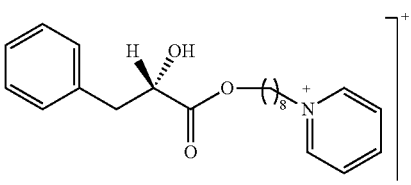
(MRS 2514)
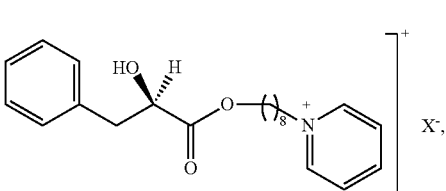
(MRS 2516)
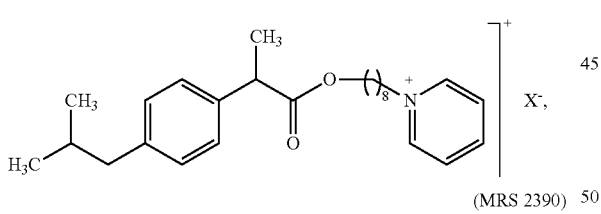
(MRS 2590)
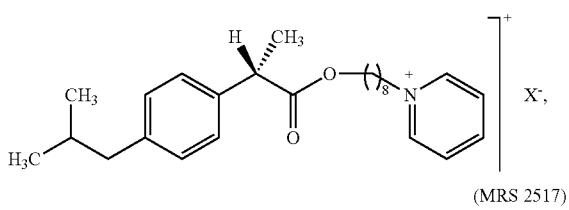
(MRS 2390)
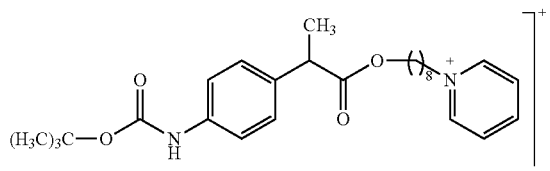
(MRS 2517)
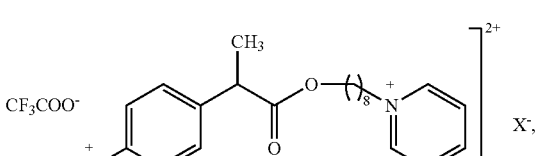
(MRS 2518)
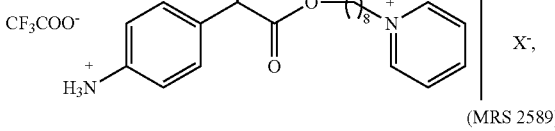
(MRS 2589)
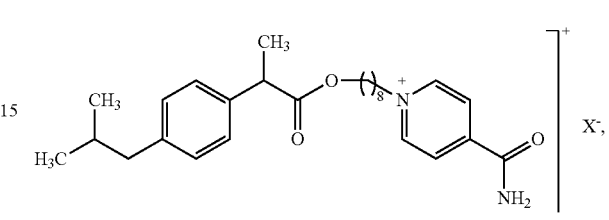
(MRS 2421)
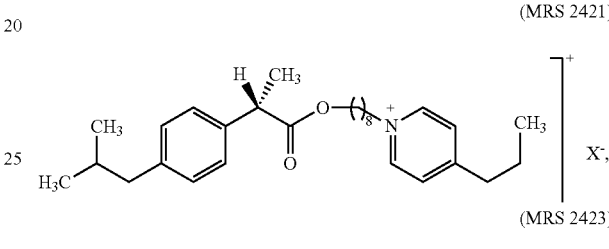
(MRS 2423)
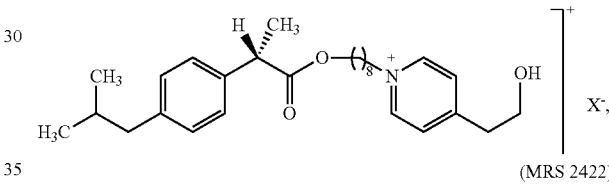
(MRS 2422)
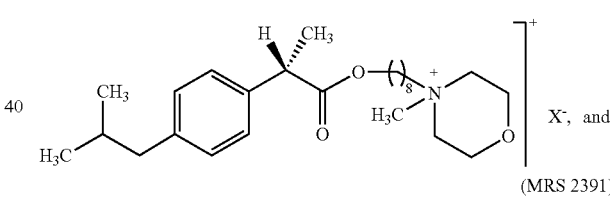
(MRS 2391)
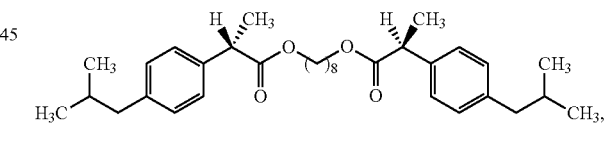
wherein X⁻ is acetate, mesylate, oxylate, chloride, bromide or iodide, and
a pharmaceutically acceptable carrier.
2. The method of treating epilepsy or related condition in a mammal according to claim 1, wherein the amphiphilic pyridinium compound is
(MRS 2481)

3. The method of treating epilepsy or related condition in a mammal according to claim 1, wherein the amphiphilic pyridinium compound is (MRS 2485)

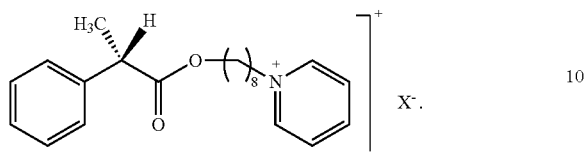

4. The method of claim 1, wherein the disease to be treated is epilepsy.

5. The method of claim 1, wherein the pharmaceutical composition is administered orally.

6. The method of claim 1, wherein the pharmaceutical composition is administered intravascularly.

7. The method of claim 1, wherein the pharmaceutical composition is administered intramuscularly.

8. The method of claim 1, wherein the pharmaceutical composition is administered subcutaneously.

9. The method of claim 8, wherein the pharmaceutical composition is administered with a penetration enhancer.

10. The method of claim 1, wherein said pharmaceutical composition is administered intraperitoneally.

11. The method of claim 1, wherein said pharmaceutical composition is administered prior to the manifestation of symptoms of epilepsy.

* * * * *

UNITED STATES PATENT AND TRADEMARK OFFICE
CERTIFICATE OF CORRECTION

PATENT NO. : 9,492,438 B2  Page 1 of 1
APPLICATION NO. : 14/808650
DATED : November 15, 2016
INVENTOR(S) : Bette Pollard It is certified that error appears in the above-identified patent and that said Letters Patent is hereby corrected as shown below:

On the Title Page

Item (54) and in the Specification, Column 1, Line 1, change "PYRIDINUM" to "PYRIDINIUM"

Signed and Sealed this
Twenty-eighth Day of February, 2017

Michelle K. Lee
*Director of the United States Patent and Trademark Office*